(12) United States Patent
O'Gara et al.

(10) Patent No.: US 10,538,492 B2
(45) Date of Patent: Jan. 21, 2020

(54) QUINOLINONE OR QUINAZOLINONE COMPRISING ANTIBIOFILM COMPOSITIONS, COMPOUNDS AND METHODS AND USES RELATING THERETO

(71) Applicant: University College Cork—National University of Ireland, Cork (IE)

(72) Inventors: Fergal O'Gara, Cork (IE); Jerry F. Reen, Cork (IE); Gerard McGlacken, Galway (IE)

(73) Assignee: University of College Cork—National University of Ireland, Cork (IE)

( * ) Notice: Subject to any disclaimer, the term of this patent is extended or adjusted under 35 U.S.C. 154(b) by 0 days.

(21) Appl. No.: 15/745,632

(22) PCT Filed: Aug. 1, 2016

(86) PCT No.: PCT/EP2016/068355
§ 371 (c)(1),
(2) Date: Jan. 17, 2018

(87) PCT Pub. No.: WO2017/021382
PCT Pub. Date: Feb. 9, 2017

(65) Prior Publication Data
US 2018/0201583 A1    Jul. 19, 2018

(30) Foreign Application Priority Data

Jul. 31, 2015 (GB) .................... 1513614.6

(51) Int. Cl.
*C07D 215/233* (2006.01)
*C07C 215/38* (2006.01)
(Continued)

(52) U.S. Cl.
CPC .......... *C07D 215/233* (2013.01); *A61P 31/00* (2018.01); *C07C 215/38* (2013.01); *C07D 239/91* (2013.01)

(58) Field of Classification Search
None
See application file for complete search history.

(56) References Cited

U.S. PATENT DOCUMENTS 5,179,107 A    1/1993    Afonso et al.

FOREIGN PATENT DOCUMENTS

| CN | 101845021 A | 9/2010 |
| CN | 104710369 A | 6/2015 |
| WO | WO-2002/018342 A2 | 3/2002 |

OTHER PUBLICATIONS

Reen, F. Organic & Biomolecular Chemistry (2012), 10(44), 8903-8910.*

(Continued)

Primary Examiner — Heidi Reese
(74) Attorney, Agent, or Firm — Howson & Howson LLP

(57) ABSTRACT

An antibiofilm composition comprising a compound of formula (A1), (A2) or (A3):

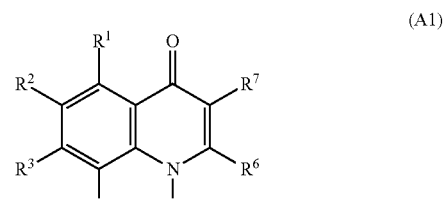

(A1)

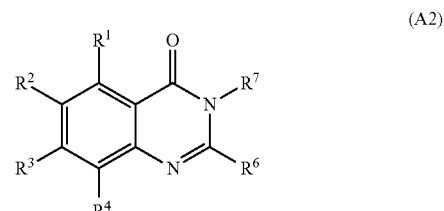

(A2)

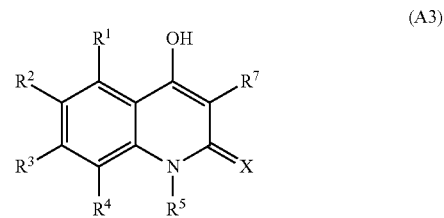

(A3)

wherein each of $R^1$, $R^2$, $R^3$, $R^4$, $R^5$, $R^6$ and $R^7$ is independently selected from hydrogen, alkyl, alkenyl, aryl, halo, alkoxy, hydroxyl, amino, nitro, sulfoxy, thiol, carboxy, alkyl carboxy and amido; and X may be O or S, wherein the composition does not comprise a compound of formula (B1) or (B2):

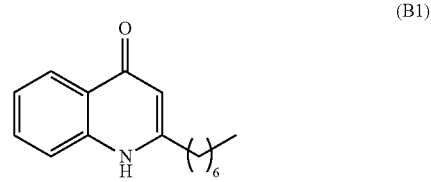

(B1)

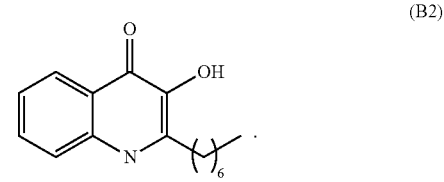

(B2)

13 Claims, 6 Drawing Sheets

(51) Int. Cl.
*C07D 239/91* (2006.01)
*A61P 31/00* (2006.01)

(56) References Cited

OTHER PUBLICATIONS

Nathubhai, A. et al., Org. Biomol. Chem. 2011 vol. 9 pp. 6089-6099.*
CAPLUS 1981:156878.*
Lu et al., "Discovery of Antagonists of PqsR, a Key Player in 2-Alkyl-4-quinolone-Dependentin", Chemistry and Biology, vol. 19(3):381-390, Jan. 2012.
Lu et al., "Optimization of anti-virulence PqsR antagonists regarding aqueous solubility and biological properties resulting in new insights in structure-activity relationships", European Journal of Medicinal Chemistry, vol. 79:173-183, May 2014.
Lu et al., "Overcoming the Unexpected Functional Inversion of a PqsR Antagonist in Pseudomonas aeruginosa: An In Vivo Potent Antivirulence Agent Targeting pqs Quorum Sensing", Angewandte Chemie International Edition, vol. 53(4):1109-1112, Dec. 2013.
Lu et al., "Supplemental Information Discovery of Antagonists of PqsR, a Key Player in 2-Alkyl-4-quinolone-Dependent Quorum Sensing in Pseudomonas aeruginosa Table S1, related to Table 1. Agonistic and Antagonistic Activities of PQS Analogues Table S2, related to Table 1. Determination of Water Solubility Table", Chemistry & Biology, Mar. 2012.
Ilangovan et al., "Structural basis for native agonist and synthetic inhibitor recognition by the Pseudomonas aeruginosa quorum sensing regulator PqsR (MvfR)", PLoS Pathogens, vol. 9(7):1-17, e1003508, Jul. 2013.
Kilani-Feki et al., "Correlation between synthesis variation of 2-alkylquinolones and the antifungal activity of burkholderia cepacian strain collection", World Journal of Microbiology & Biotechnology, vol. 28(1):275-281, Jun. 2012.
Lu et al., "Discovery of antagonists of PqsR, a key player in 2-alkyl-4-quinolone-dependent quorum sensing in Pseudomonas aeruginosa", Chemistry & Biology, vol. 19:381-390, Mar. 2012.
Reen et al., "A structure activity-relationship study of the bacterial signal molecule HHQ reveals swarming motility inhibition in Bacillus atrophaeus", Organic & Biomolecular Chemistry, vol. 13(19):5537-5541, Jan. 2015.
Reen et al., "Structure-function analysis of the C-3 position in analogues of microbial behavioural modulators HHQ and PQS", Organic & Biomolecular Chemistry, vol. 10(44):8903, Jan. 2012.
Reen et al., "The Pseudomonas quinolone signal (PQS), and its precursor HHQ, modulate interspecies and interkingdom behavior", Fems Microbiology Ecology, vol. 77(2):413-428, May 2011.
Tang et al., "Design, synthesis and biological evaluation of novel non-azole derivatives as potential antifungal agents", Chinese Chemical Letters, vol. 26(9):1161-1164, Apr. 2015.
Search Report issued on UK priority application No. GB1513614.6, dated May 11, 2016.
International Search Report issued on parent International Patent Application No. PCT/EP2016/068355, dated Nov. 28, 2016.
Tunney et al., "Rapid Colorimetric Assay for Antimicrobial Susceptibility Testing of Pseudomonas aeruginosa", Antimicrobial Agents and Chemotherapy, vol. 48(5):1879-1881, May 2004.
International Preliminary Report on Patentability issued on priority International Application No. PCT/EP2016/068355, dated Feb. 6, 2018.

* cited by examiner

C1

C2

C7

C8

C9

C10

QUINOLINONE OR QUINAZOLINONE COMPRISING ANTIBIOFILM COMPOSITIONS, COMPOUNDS AND METHODS AND USES RELATING THERETO

The present invention relates to methods of combating biofilms and in particular biofilms caused by fungal infection. The invention also relates to compositions and novel compounds for use in such methods. The invention finds particular utility in combatting fungal infections in medical devices, for example implanted medical devices.

Implanted medical devices are extremely important and widely used in modern medicine, saving lives and improving the quality of life of millions of people throughout the world. However negative outcomes following implantation can occur due to microbial infection. Failure to effectively treat such infections can lead to serious illness and even death. In many cases conventional therapies fail and the only treatment option is removal of the device.

Treatment of microbial infection with conventional antibiotics and antimycotics is increasingly difficult due to the continuing emergence of resistant microbes.

Many pathogens can enter the biofilm mode of growth. A biofilm is formed when microbes form a structured community of cells. Biofilms play a key role in enabling a pathogen to overcome host defenses and contribute to its virulence. Pathogens which enter the biofilm mode of growth may emerge post treatment as resistant strains that can propagate freely and are recalcitrant to conventional therapies.

In addition to infection of biomedical implants, biofilm formation contributes to other serious infections including antibiotic resistant infections in hospitals and contamination of pharmaceutical formulations.

The present invention seeks to provide means for disrupting biofilm formation and growth, and in particular biofilm formation due to fungal infection. The present invention also provides means for combatting fungal infection, especially fungal infection due to *Candida albicans* or *Aspergillus fumigatus*. Fungal infection can cause serious illness, especially in patients with compromised immune systems.

The development of antibiotics has slowed significantly in recent years and there is an increasing awareness of the hazards associated with the use of antibiotic and chemical agents. There is thus an urgent need for new, more effective therapies.

However when developing new therapeutic compounds it is important to consider all effects that the compounds may have in a biological environment. For example some compounds are known to have antifungal properties but are also known agonists for some bacterial species, for example *Pseudomonas aeruginosa*. It is also necessary to ensure that compounds intended for medical use are not cytotoxic to human cells.

Figure 1:
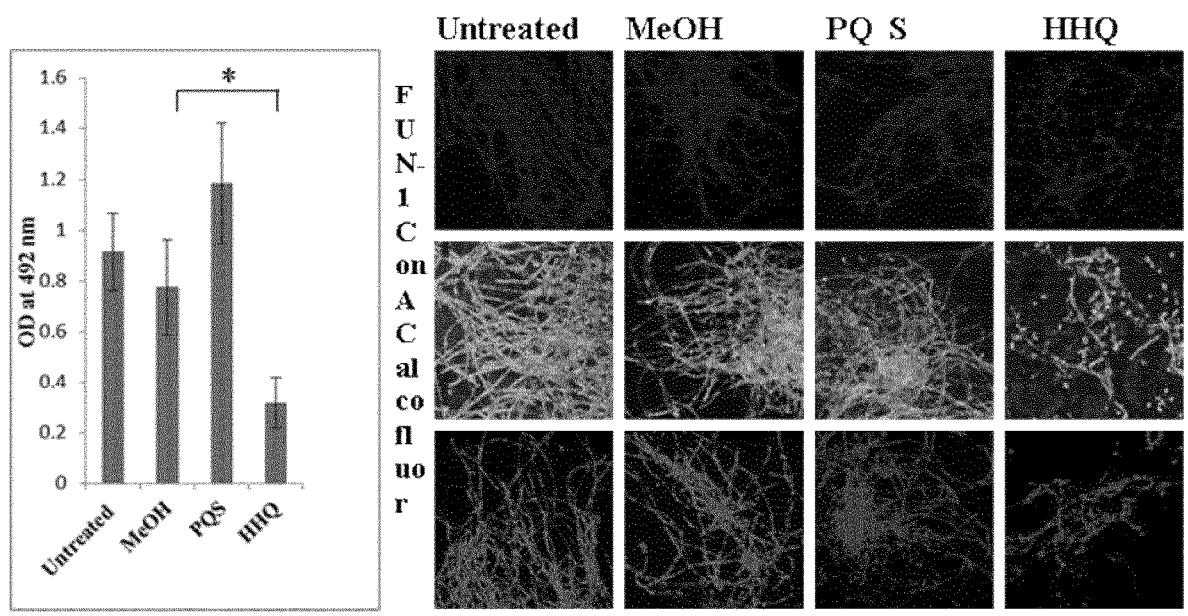
FIG. 1 shows graphically the XTT results for compounds B1, B2, methanol (i.e. the solvent alone) and untreated biofilms.

According to a first aspect of the present invention there is provided an antibiofilm composition comprising a compound of formula (A1), (A2) or (A3):

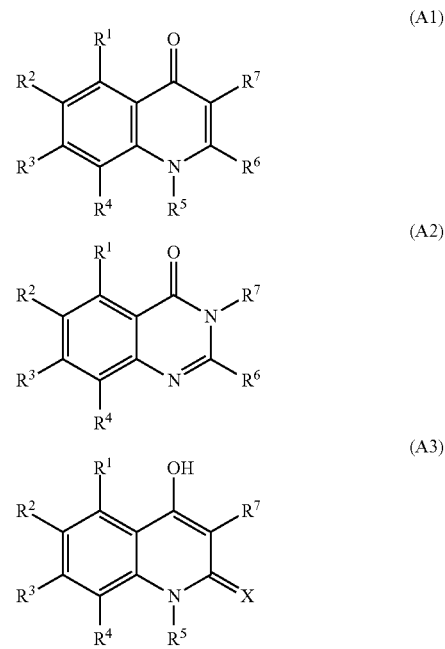

wherein each of $R^1$, $R^2$, $R^3$, $R^4$, $R^5$, $R^6$ and R is independently selected from hydrogen, alkyl, alkenyl, aryl, halo, alkoxy, hydroxyl, amino, nitro, sulfoxy, thiol, carboxy, alkyl carboxy and amido; and X may be O or S, wherein the composition does not comprise a compound of formula (B1) or (B2):

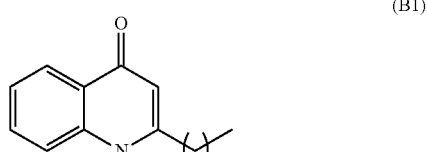

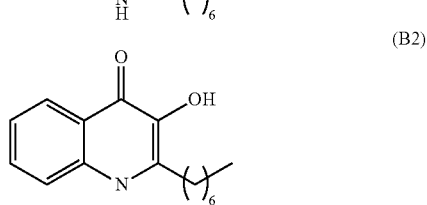

By carboxy substituent we mean to refer to the group $COO^-Y^+$ wherein Y is $H^+$ or a metal or ammonium ion, for example $Na^+$, $K^+$ or $NH_4^+$.

By alkyl carboxy substituent we mean to refer to the group $COOR^8$ wherein $R^8$ is alkyl. Preferred alkyl carboxy groups includes $CO_2Me$ and $CO_2Et$.

By amido substituent we mean to refer to the group $NHCOR^9$ where $R^9$ is an alkyl, alkenyl or aryl group. Preferably $R^9$ is an alkyl group, suitably a $C_1$ to $C_4$ alkyl group.

When $R^1$, $R^2$, $R^3$, $R^4$, $R^5$, $R^6$ and $R^7$ is an alkyl, alkenyl or aryl substituent these groups may be straight chain or branched or may themselves be substituted. Unsubstituted alkyl, alkenyl and aryl groups are preferred.

Suitable alkyl, alkenyl and aryl groups may have up to 30 carbon atoms, preferably up to 20 carbon atoms, preferably up to 16 carbon atoms, for example up to 12 carbon atoms or up to 8 carbon atoms.

When $R^1$, $R^2$, $R^3$, $R^4$, $R^5$, $R^6$ and $R^7$ is an alkyl or alkenyl substituent it may be straight chain or branched.

In some embodiments two substituents may be linked to form a cyclic alkyl or aryl group.

Each of $R^1$, $R^2$, $R^3$, $R^4$, $R^5$, $R^6$ and $R^7$ may independently be halo. Suitable halo groups include fluoro, bromo and chloro. Chloro substituents are especially preferred.

Each of $R^1$, $R^2$, $R^3$, $R^4$, $R^5$, $R^6$ and $R^7$ may be an alkoxy group. Preferred alkoxy groups are methoxy groups.

Suitably each of $R^1$, $R^2$, $R^3$, $R^4$, $R^5$, $R^6$ and $R^7$ is selected from hydrogen, alkyl, alkoxy, halo and amino. Suitably each of $R^1$, $R^2$, $R^3$, $R^4$, $R^5$, $R^6$ and $R^7$ is selected from hydrogen, $C_1$ to $C_8$ alkyl, methoxy, chloro and amino.

Preferably at least one of $R^1$, $R^2$, $R^3$, $R^4$, $R^5$, $R^6$ and $R^7$ is not hydrogen.

$R^1$ may be selected from hydrogen, alkyl, alkenyl, aryl, halo, alkoxy, hydroxyl, amino, nitro, sulfoxy, thiol, carboxy, amido and alkyl carboxy.

Preferably $R^1$ is selected from hydrogen, alkyl, alkoxy and halo.

Suitably $R^1$ is selected from hydrogen, methyl, methoxy and chloro. Preferably $R^1$ is hydrogen or methyl. Most preferably $R^1$ is hydrogen.

$R^2$ may be selected from hydrogen, alkyl, alkenyl, aryl, halo, alkoxy, hydroxyl, amino, nitro, sulfoxy, thiol, carboxy, amido and alkyl carboxy.

Preferably $R^2$ is selected from hydrogen, alkyl, alkoxy, halo and alkyl carboxy.

Suitably $R^2$ is selected from hydrogen, $C_1$ to $C_8$ alkyl, methoxy, fluoro, bromo, chloro and $CO_2R^8$ wherein $R^8$ is $C_1$ to $C_4$ alkyl.

Suitably $R^2$ is selected from hydrogen, methyl, t-butyl, n-hexyl, methoxy, fluoro, bromo, chloro and $CO_2Et$. Preferably $R^2$ is selected from hydrogen, methyl, n-hexyl, chloro and methoxy.

$R^3$ may be selected from hydrogen, alkyl, alkenyl, aryl, halo, alkoxy, hydroxyl, amino, nitro, sulfoxy, thiol, carboxy, amido and alkyl carboxy.

Preferably $R^3$ is selected from hydrogen, alkyl, aryl and alkoxy.

Suitably $R^3$ is selected from hydrogen, methyl and methoxy.

In some embodiments $R^3$ and $R^4$ may together form a group of formula —CH—CH—CH—CH— i.e., they form a further fused benzene ring. This further benzene ring may itself be substituted.

Preferably $R^3$ is hydrogen or methoxy.

$R^4$ may be selected from hydrogen, alkyl, alkenyl, aryl, halo, alkoxy, hydroxyl, amino, nitro, sulfoxy, thiol, carboxy, amido and alkyl carboxy.

Preferably $R^4$ is selected from hydrogen, alkyl, aryl, halo and alkoxy.

Suitably $R^4$ is selected from hydrogen, methoxy and chloro.

In some embodiments $R^3$ and $R^4$ together form a group of formula —CH—CH—CH—CH— i.e., they form a further fused benzene ring. This further benzene ring may itself be substituted.

Preferably $R^4$ is hydrogen or chloro.

$R^5$ may be selected from hydrogen, alkyl, alkenyl aryl, halo, alkoxy, hydroxyl, amino, nitro, sulfoxy, thiol, carboxy, amido and alkyl carboxy. Preferably $R^5$ is hydrogen or alkyl.

When the invention comprises a compound of formula (A1) $R^5$ may suitably be hydrogen or alkyl. Preferred alkyl groups are $C_1$ to $C_{12}$ alkyl groups, preferably $C_4$ to $C_{12}$ alkyl, more preferably $C_6$ to $C_{10}$, for example $C_7$ to $C_9$ alkyl groups. These groups may be straight chain or branched and may be substituted. Preferred are unsubstituted alkyl groups.

Preferably $R^5$ is hydrogen or $C_7$ to $C_9$ alkyl. Suitably $R^5$ is hydrogen.

When the invention comprises a compound of formula (A3) $R^5$ may suitably be hydrogen or alkyl. Preferably it is alkyl. Preferably $R^5$ is $C_1$ to $C_{20}$ alkyl, more preferably $C_4$ to $C_{12}$ alkyl, more preferably $C_6$ to $C_{10}$ alkyl, for example $C_7$ to $C_9$ alkyl. These alkyl groups may be straight chain or branched and may be substituted. Preferred are unsubstituted alkyl groups.

$R^6$ may be selected from hydrogen, alkyl, alkenyl, aryl, halo, alkoxy, hydroxyl, amino, nitro, sulfoxy, thiol, carboxy and alkyl carboxy.

Preferably $R^6$ is alkyl. Most preferably $R^6$ is a $C_1$ to $C_{24}$ alkyl group, preferably a $C_2$ to $C_{16}$ alkyl group, more preferably a $C_{14}$ to $C_{16}$ alkyl group, more preferably a $C_4$ to $C_{12}$ alkyl group, especially a $C_6$ to $C_{10}$ alkyl group, for example a $C_7$ to $C_9$ alkyl group. The alkyl may be straight chain or branched. It may itself be substituted. Preferably $R^6$ is an unsubstituted alkyl group. Preferably it is straight chain. Suitably $R^6$ is an alkyl group of formula $(CH_2)_nCH_3$ wherein n is from 3 to 15, preferably from 4 to 12, more preferably from 5 to 10, most preferably from 6 to 8. Preferably n is 6 or 8.

$R^7$ may be selected from hydrogen, alkyl, alkenyl, aryl, halo, alkoxy, hydroxyl, amino, nitro, sulfoxy, thiol, carboxy, amido and alkyl carboxy.

When the invention comprises a compound of formula (A1) or (A3) $R^7$ is preferably hydrogen.

When the invention comprises a compound of formula (A2) $R^7$ is preferably hydrogen or amino ($NH_2$).

X may be O or S. Preferably X is O.

In some embodiments $R^1$ is hydrogen or methyl; $R^2$ is hydrogen, $C_1$ to $C_8$ alkyl, halo or alkoxy; $R^3$ is hydrogen, alkyl or alkoxy; $R^4$ is hydrogen or halo; $R^5$ is hydrogen or alkyl; $R^6$ is alkyl; $R^7$ is hydrogen or amino and X is O.

In some embodiments $R^1$ is hydrogen; $R^2$ is hydrogen, methoxy or chloro; $R^3$ is hydrogen or methoxy; $R^4$ is hydrogen or chloro; $R^5$ is hydrogen or $C_4$ to $C_{10}$ alkyl; $R^6$ is $C_5$ to $C_{12}$ alkyl, preferably $C_7$ to $C_9$ alkyl; $R^7$ is hydrogen or amino; and X is O.

In some preferred embodiments the composition comprises a compound selected from:

(i) a compound of formula (A1) in which $R^1$ is hydrogen or methyl; $R^2$ is hydrogen, $C_1$ to $C_6$ alkyl, alkoxy, halo or $CO_2Et$; $R^3$ is hydrogen, methyl or methoxy or an aryl group with $R^4$; $R^4$ is hydrogen, methoxy, chloro or an aryl group with $R^3$; $R^5$ is hydrogen; $R^6$ is $C_6$ to $C_{10}$ alkyl; and $R^7$ is hydrogen;

(ii) a compound of formula (A2) wherein $R^1$ is hydrogen or methyl; $R^2$ is hydrogen, $C_1$ to $C_6$ alkyl halo or $CO_2Et$; $R^3$ is hydrogen, methyl or methoxy or an aryl group with $R^4$; $R^4$ is hydrogen, methoxy, chloro or an aryl group with $R^3$; $R^6$ is $C_6$ to $C_{10}$ alkyl and $R^7$ is hydrogen or amino; and (iii) a compound of formula (A3) wherein $R^1$ is hydrogen or methyl; $R^2$ is hydrogen, $C_1$ to $C_6$ alkyl, halo or $CO_2Et$; $R^3$ is hydrogen, methyl or methoxy or an aryl group with $R^4$; $R^4$ is hydrogen, methoxy, chloro or an aryl group with $R^3$; $R^5$ is $C_6$ to $C_{10}$ alkyl; $R^7$ is hydrogen and X is O or S.

In some preferred embodiments the composition comprises a compound selected from:

(i) a compound of formula (A1) in which $R^1$ is hydrogen or methyl; $R^2$ is hydrogen, $C_1$ to $C_6$ alkyl, chloro or methoxy; $R^3$ is hydrogen; $R^4$ is hydrogen or chloro; $R^5$ is hydrogen; $R^6$ is $C_7$ to $C_9$ alkyl; and $R^7$ is hydrogen;

(ii) a compound of formula (A2) wherein $R^1$ is hydrogen; $R^2$ is hydrogen; $R^3$ is hydrogen; $R^4$ is hydrogen; $R^6$ is $C_7$ to $C_9$ alkyl; and $R^7$ is hydrogen or amino; and (iii) a compound of formula (A3) wherein $R^1$ is hydrogen; $R^2$ is hydrogen; $R^4$ is hydrogen; $R^5$ is $C_7$ to $C_9$ alkyl; $R^7$ is hydrogen and X is O.

Some especially preferred compounds for use in the invention structures have the following structures:

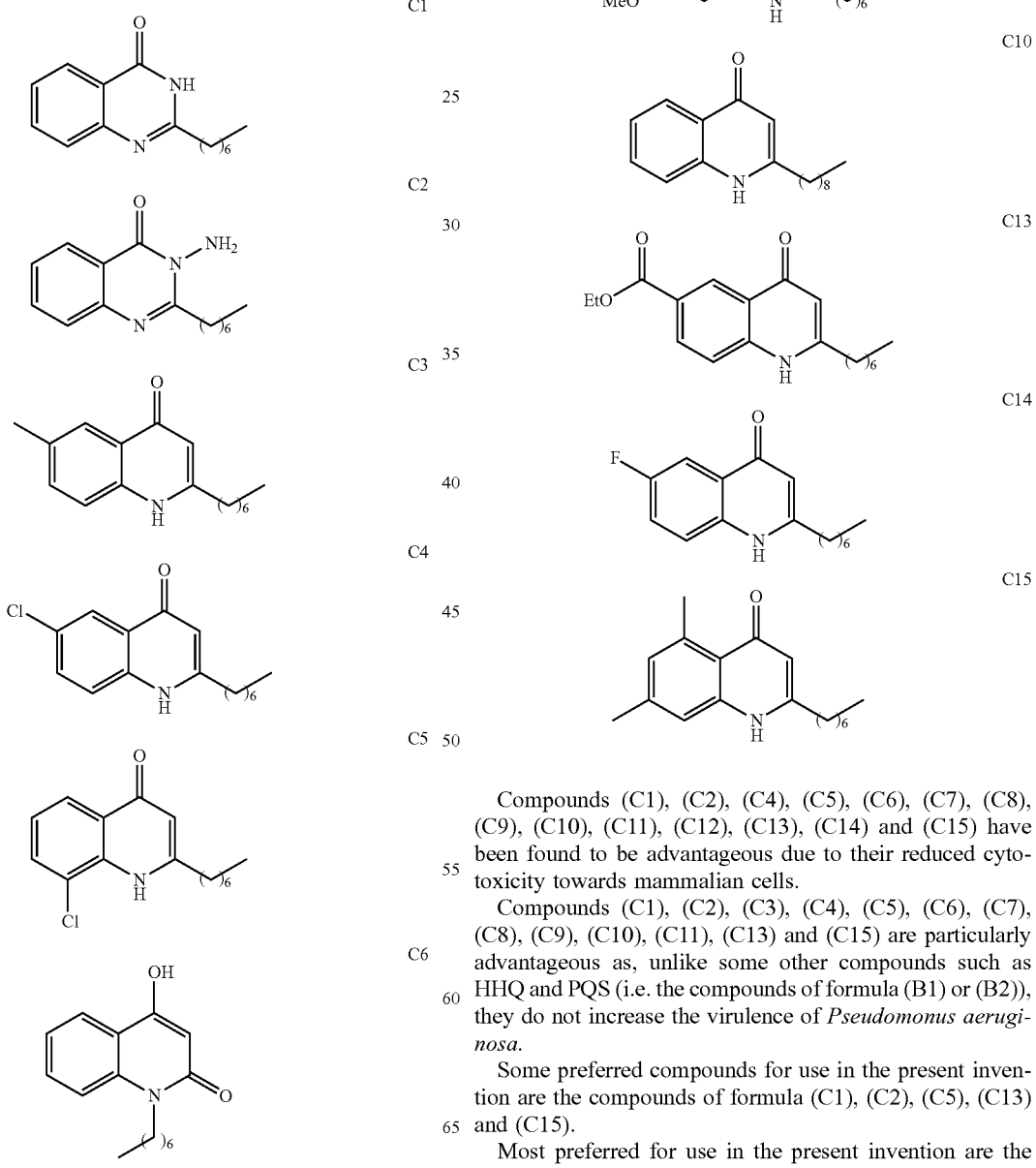

Compounds (C1), (C2), (C4), (C5), (C6), (C7), (C8), (C9), (C10), (C11), (C12), (C13), (C14) and (C15) have been found to be advantageous due to their reduced cytotoxicity towards mammalian cells.

Compounds (C1), (C2), (C3), (C4), (C5), (C6), (C7), (C8), (C9), (C10), (C11), (C13) and (C15) are particularly advantageous as, unlike some other compounds such as HHQ and PQS (i.e. the compounds of formula (B1) or (B2)), they do not increase the virulence of *Pseudomonus aeruginosa*.

Some preferred compounds for use in the present invention are the compounds of formula (C1), (C2), (C5), (C13) and (C15).

Most preferred for use in the present invention are the compounds of formula (C1), (C2) and (C5).

The composition of the first aspect is an anti-biofilm composition. By anti-biofilm composition we mean to include compositions that disrupt or remove biofilms or compositions that inhibit or prevent the growth of biofilm. Preferably the composition is effective against biofilms formed by fungi. Thus the present invention suitably provides compositions that disrupt or remove fungal biofilms or inhibit or prevent the growth of fungal biofilms.

The anti-biofilm composition of the present invention may be used as a surface treatment composition. For example it may be contacted with surfaces on which fungal growth is highly undesirable, for example in a hospital, especially a surgical environment.

By "effective against" we mean has anti-biofilm activity against, as described above. The composition of the present invention is preferably effective against biofilms formed by fungal species selected from the genera *Candida* and *Aspergillus*. Preferably the composition of the first aspect is effective against biofilms formed by *Candida albicans* and/or *Aspergillus fumigatus*.

In some embodiments the compositions of the present invention are effective against *Candida albicans*. Some preferred compounds which are effective against fungal biofilms formed by *Candida albicans* are compounds of formula (A1), (A2) or (A3) wherein $R^1$ is hydrogen; $R^2$ is hydrogen, $C_1$ to $C_6$ alkyl or halo; $R^3$ is hydrogen; $R^4$ is hydrogen; $R^5$ is hydrogen or $C_6$ to $C_{10}$ alkyl; $R^6$ is $C_6$ to $C_{10}$ alkyl; $R^7$ is hydrogen or amino and X is O.

Some especially preferred compounds for use against *Candida albicans* include
(i) a compound of formula (A1) in which $R^1$ is hydrogen; $R^2$ is hydrogen, methyl or chloro; $R^3$ is hydrogen; $R^4$ is hydrogen or chloro; $R^5$ is hydrogen; $R^6$ is $C_7$ alkyl; and $R^7$ is hydrogen;
(ii) a compound of formula (A2) wherein $R^1$ is hydrogen; $R^2$ is hydrogen; $R^3$ is hydrogen; $R^4$ is hydrogen; $R^6$ is $C_7$ alkyl and $R^7$ is hydrogen or amino; and
(iii) a compound of formula (A3) wherein $R^1$ is hydrogen; $R^2$ is hydrogen; $R^3$ is hydrogen; $R^4$ is hydrogen; $R^5$ is $C_7$ alkyl; $R^7$ is hydrogen and X is O.

Some especially preferred compounds which are effective against fungal biofilms formed by *Candida albicans* are compounds having the structures (C1), (C2), (C3), (C4), (C5) and (C6).

In some embodiments the compositions of the present inventions are effective against *Aspergillus fumigatus*. Some especially preferred compounds for use against *Aspergillus fumigatus* include compounds of formula (A1), (A2) or (A3) wherein $R^1$ is hydrogen; $R^2$ is hydrogen, alkoxy or $C_1$ to $C_8$ alkyl; $R^3$ is hydrogen or alkoxy; $R^4$ is hydrogen; $R^5$ is hydrogen; $R^6$ is $C_8$ to $C_{10}$ alkyl; $R^7$ is hydrogen or amino and X is O.

Compounds of formula (A1) or (A2) are especially effective against *Aspergillus fumigatus*. In some especially preferred compounds for combatting biofilms found by *Aspergillus fumigatus* include:
(i) a compound of formula (A1) in which $R^1$ is hydrogen; $R^2$ is hydrogen, n-hexyl or methoxy; $R^3$ is hydrogen or methoxy; $R^4$ is hydrogen or chloro; $R^5$ is hydrogen; $R^6$ is $C_7$ to $C_9$ alkyl; and $R^7$ hydrogen; and
(ii) a compound of formula (A2) wherein $R^1$ is hydrogen; $R^2$ is hydrogen; $R^3$ is hydrogen; $R^4$ is hydrogen; $R^6$ is $C_7$ alkyl and $R^7$ is hydrogen or amino.

Some especially preferred compounds which are effective against fungal biofilms formed by *Aspergillus fumigatus* are compounds having the structures (C1), (C2), (C4), (C7), (C8), (C9), (C10), (C13) and (C15).

In some embodiments the composition of the first aspect may be a pharmaceutical preparation comprising a compound of formula (A1), (A2) or (A3). Preferred features of the compound are as described above.

The pharmaceutical preparation may be provided in any suitable form. For example in some embodiments the pharmaceutical preparation may be provided in the form of a gel, cream or paste suitable for topical application.

In some embodiments the pharmaceutical preparation may be in the form of a tablet, syrup or powder suitable for oral delivery.

In some embodiments the pharmaceutical preparation may be provided as a solution suitable for intravenous infusion or injection.

In some embodiments it is provided in a form suitable for inhalation. The pharmaceutical preparation may be provided in a form suitable for delivery as a suppository or for subcutaneous delivery. It may be provided on a patch. Other suitable forms will be known to the person skilled in the art.

The pharmaceutical preparation may include a diluent or carrier and one or more further excipients. Suitable diluents, carriers and further excipients will depend on the form of a pharmaceutical preparation and the intended delivery method. The selection of suitable diluents, carriers and excipients is within the competence of the person skilled in the art.

The compound (A1), (A2) or (A3) is may suitably be included in a pharmaceutical preparation in an amount of from 0.1 to 100 µg/ml, for example from 1 to 50 µg/ml. However the selection of appropriate dosage rate and suitable delivery method will be within the competence of the skilled person.

The composition of the first aspect may be provided in many different forms depending on the intended use thereof.

In some embodiments the composition may be a pharmaceutical preparation as defined above.

In some embodiments the composition may be a disinfectant composition. A disinfectant composition may suitably be provided as a gel, paste, aerosol or solution. It may be provided as a powder, tablet or granules or concentrated composition to be diluted prior to use.

In some embodiments the composition of the first aspect may be a coating composition. Suitable ingredients for inclusion in such a composition will be known to the person skilled in the art.

According to a second aspect of the present invention there is provided a method of combatting a biofilm at a locus, the method comprising contacting the locus with a composition of the first aspect.

By combatting biofilms we mean to include disrupting or removing biofilms and inhibiting or preventing the growth of biofilms. In particular the method of the second aspect is a method of combatting fungal biofilms.

By fungal biofilms we mean to include any biofilm which includes one or more species of fungus growing in the biofilm mode. The fungal biofilm may contain only a single fungal species or it may also contain one or more other microbes, for example one or more further species of fungui and/or bacteria.

Preferred features of the second aspect are as defined in relation to the first aspect and features described in relation to the second aspect also apply to first aspect.

The method of the second aspect may be a method of disinfecting or sterilising a surface. Suitably the method disrupts any fungal biofilm attached to or growing on the surface. It may remove existing biofilms, disrupt existing biofilms and/or the method may prevent or inhibit the formation or growth of fungal biofilms at the surface.

In some embodiments the method of the second aspect may provide a method of treating a medical device, the method comprising contacting the device with a composition of the first aspect. The method may be used with any suitable medical device, including surgical instruments, diagnostic equipment and implanted devices.

The composition may be contacted with the device by any suitable means. For example the composition may be sprayed, wiped or painted onto the device or the device could be immersed in the composition. In some embodiments the composition may provide a polymeric coating on the device.

For example the present invention may provide a method of disinfecting a clinical scope, for example an endoscope, the method comprising contacting the scope with a composition of the first aspect.

In some embodiments the method of the second aspect may be a method of treating contact lenses, the method comprising immersing the contact lenses in a composition of the first aspect.

Thus the composition of the first aspect may be a contact lens solution.

It is currently very difficult to eliminate fungal biofilm growth on contact lenses using conventional antimicrobial agents. This can lead to contact lens wearers developing very uncomfortable fungal eye infections. Thus the method of the present aspect of the invention is highly beneficial.

The method of the second aspect is a method of combatting biofilms, preferably fungal biofilms at a locus. The locus may be the surface of an inanimate object—or it may be a location within the body of an animal, suitably a human.

The method of the second aspect suitably involves combatting fungi selected from *Candida albicans* and/or *Aspergillus fumigatus*.

The composition of the first aspect of the present invention may be used in a wide variety of applications. The amount of the compounds of formula (A1), (A2) or (A3) that should be included in the composition and the further components of the composition will depend on the intended use of the composition. However the selection of appropriate amounts of the active compounds and suitable further components is within the competence of the person skilled in the art.

According to a third aspect of the present invention there is provided a compound of formula (A1), (A2) or (A3) for use in the treatment of a fungal biofilm infection. Preferred features of the third aspect are as defined in relation to the first and second aspects.

Current treatment options for fungal biofilm-related infections are limited by the intrinsic tolerance of biofilms to anti-fungal antibiotics, otherwise known as antimycotics, whereby the biofilm effectively shields the microbe from the active agent. In addition, changes to the physiology of the cell within the biofilm can also contribute to the intrinsic resistance reported towards antibiotics. While there has been some limited success with conventional antibiotics, e.g. liposomal amphotericin B, reports of resistance continue to emerge with the biofilm mode of growth a primary factor underpinning resistance to conventional antimicrobial agents.

The compositions of the present invention help to disrupt biofilms or prevent or inhibit the growth of biofilms. This may allow conventional agents to attack microbes and kill them.

Thus the present invention may provide a combination of a compound of formula (A1), (A2) or (A3) and one or more further antimicrobial agents for use in the treatment of a fungal biofilm infection.

The composition of the first aspect may in some embodiments comprise a compound of formula (A1), (A2) or (A3) and one or more further antimicrobial agents.

Suitably the one or more further antimicrobial agents is an antifungal agent. Suitable antifungal agents include fluconazole, amphotericin B and nystatin.

The present invention may provide a compound of formula (A1), (A2) or (A3) for use in the treatment of a fungal biofilm infection caused by a fungus selected from *Aspergillus fumigatus, Candida albicans* and/or mixtures thereof.

The third aspect of the present invention may provide a compound of formula (A1), (A2) or (A3) for use in the treatment of a fungal biofilm infection caused by *Aspergillus fumigatus*. Compounds particularly effective for use in the treatment of a fungal biofilm infection with *Aspergillus fumigatus* are as defined in relation to the first aspect.

The third aspect of the present invention may provide the use of a compound of formula (A1), (A2) or (A3) for use in the treatment of a fungal biofilm infection caused by *Candida albicans*. Compounds especially suitable for use in such treatment are as defined in relation to the first aspect.

As such the present invention provides a significant advancement in the potential prevention of serious illness and possibly fatalities due to infection with fungal biofilms. Fungal biofilms caused by *Candida albicans* and *Aspergillus fumigatus* can lead to serious infections in implanted medical devices. They are also commonly associated with hospital acquired infections and contamination of pharmaceutical formulations. For example biofilms on medical devices used to treat more than one patient may not be effectively removed by conventional sterilisation techniques.

Infection with fungi that form biofilms can cause very serious illness and even death, especially in patients with other conditions and/or weakened immune systems. *Aspergillus fumigatus* for example can form biofilms within the lungs of a patient. Once the biofilm has formed it is very difficult for the infection to be treated. Conventional antimicrobial agents are often ineffective in such circumstances.

However the compositions of the present invention have been found to be able to disrupt fungal biofilms and thus may be used in the treatment of patients having a fungal biofilm infection, for example associated with a respiratory disease. Patients with, for example, cystic fibrosis are vulnerable to infection with fungal biofilms.

Thus the present invention may provide compounds of formula (A1), (A2) and (A3) for use in the treatment of a respiratory disease.

In some embodiments the invention may provide compounds of formula (A1), (A2) and (A3) for use in the treatment of cystic fibrosis.

The invention may suitably provide compounds of formula (A1), (A2) or (A3) for use in the disruption or prevention of a fungal biofilm infection.

The present invention may be useful in the treatment of infections caused by fungal biofilms. The invention may also be used to prevent or inhibit the growth of fungal biofilms. Thus the present invention may provide a prophylactic treatment.

According to a fourth aspect of the present invention there is provided a medical device having a coating on at least a portion thereof; wherein the coating comprises a compound of formula (A1), (A2) or (A3).

Preferred features of the fourth aspect are as defined in relation to the first, second and third aspects.

The medical device of the present invention may be selected from a wide range of medical devices. Suitable medical devices include prosthetic limbs, hip replacement joints, stents, catheters, medical scopes and contact lenses.

According to a fifth aspect of the present invention there is provided a compound of formula (A3):

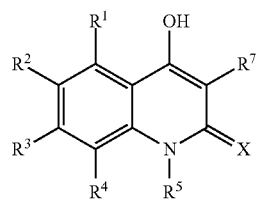

(A3)

Preferred features of the fifth aspect are as defined in relation to the first, second, third and fourth aspects.

According to a sixth aspect of the present invention there is provided a method of preparing a compound of formula (A3).

Any suitable method may be used. One suitable method involves stirring an anthranilic acid with an alkyl halide (for example bromoheptane) in base at elevated temperature. The resultant secondary amine product is heated with acetic anhydride in acid. Work-up provides the crude 2-quinolones which may be purified by recrystallization.

In an alternative method an aniline may be heated with dimethylsulphate in base and an alkylhalide (for example bromoheptane) was added. The resultant secondary amine product may be heated with Meldrum's acid followed by addition of Eaton's reagent. Work-up and purification using chromatography gives the target 2-quinolones of formula (A3).

According to a seventh aspect of the present invention there is provided a compound of formula (A3) for use in therapy.

The present invention may further provide compounds of formula (A3) for use in the treatment of a fungal biofilm infection.

Suitably the present invention provides compounds of formula (A3) for use in the treatment of a biofilm infection caused by *Aspergillus fumigatus* and/or *Candida albicans*.

In some embodiments the present invention provides compounds of formula (A3) for use in the treatment of a biofilm infection caused by *Candida albicans*.

The present invention will now be further described with reference to the following non-limiting examples.

EXAMPLE 1

The following compounds were prepared using the methods described in Org. Biomol. Chem., 2015, 13, 5537-5541 and analogous processes:

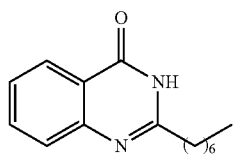

C1

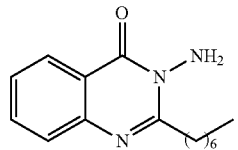

C2

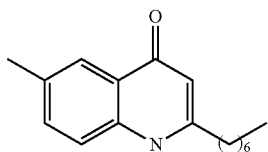

C3

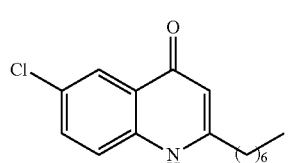

C4

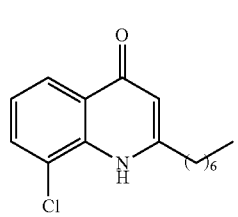

C5

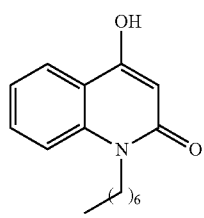

C6

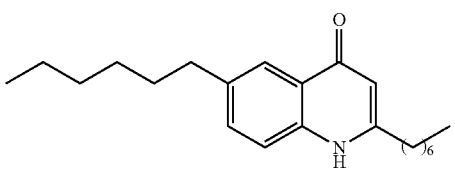

C7

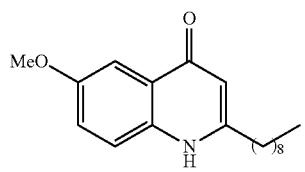

C8

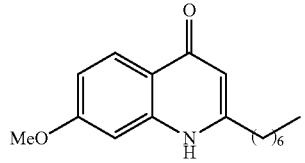

C9

C10
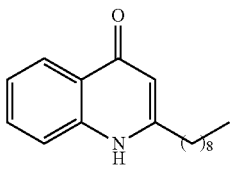

C11
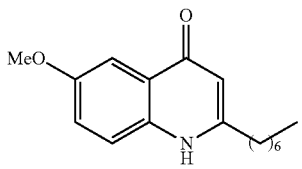

C12
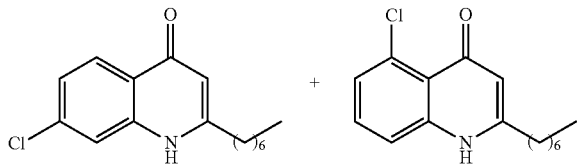

C13
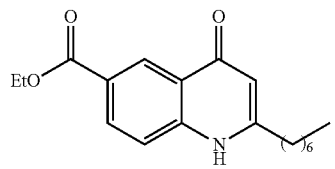

C14
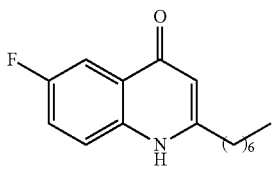

C15
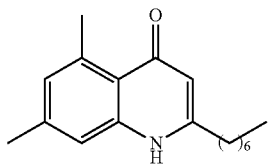

The properties of these compounds were tested and compared to the properties of:

(B1)
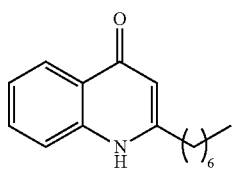

(B2)
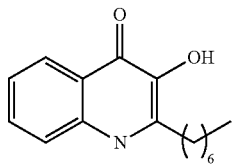

The following general conditions were used in the biological testing of some of the above compounds to assess their effectiveness against *Candida albicans*:

*C. albicans* Stock Maintenance and Culturing Conditions.

*C. albicans* strain SC5314 was sub-cultured from 15% (v/v) glycerol stocks at −80° C. onto Yeast Peptone Dextrose (YPD) medium [1% (w/v) yeast extract, 2% (w/v) peptone and 2% (w/v) dextrose] and incubated at 30° C. overnight.

*P. aeruginosa* Stock Maintenance and Culturing Conditions.

*P. aeruginosa* strains, PAO1 and pqsA mutant, containing the chromosomally inserted pqsA-lacZ promoter fusion on plasmid pUC18-mini-Tn7, were sub-cultured from glycerol stocks onto LB agar plates, supplemented with Carbenicillin (200 μg/ml) and X-gal (40 μg/ml), and incubated at 37° C. overnight. Single colonies were inoculated into LB broth (20 ml), supplemented with Carbenicillin (200 μg/ml), and incubated at 37° C., shaking at 180 rpm overnight. For subsequent experiments, the $OD_{600nm}$ was recorded and a starting $OD_{600}$ nm of 0.02 was inoculated into fresh LB broth, supplemented with Carbenicillin (200 μg/ml) and incubated at 37° C., shaking at 180 rpm.

Test Compounds

The test compounds in desiccated form were re-suspended in Methanol to create a 10 mM stock. A working concentration of 100 μM was used in all experiments.

TLC Analysis.

Silica TLC plates, activated by soaking in 5% (w/v) $K_2HPO_4$ for 30 min were placed in an oven at 100° C. for 1 hr. Test compounds (5 μl, 10 mM) were spotted approximately 1 cm from the bottom. The spots were dried and the plate placed in a mobile phase comprising 95:5 dichloromethane:methanol. The plate was viewed under UV light when the mobile phase had run 5 cm below the top of the plate.

EXAMPLE 2

The ability of some of the compounds detailed in example 1 to disrupt *Candida albicans* was tested using Confocal Scanning Laser Microscopy and an XTT Metabolic Assay. The XTT assay is a commonly used quantitative method assessing *Candida* biofilm mass and growth often in response to novel drug therapies.

*C. albicans* biofilm formation was carried out in 96 well plates by a method of the prior art. Briefly, *C. albicans* was inoculated into Yeast Nitrogen Base [10% (w/v)] and glucose/maltose [10% (w/v)] and incubated overnight at 30° C. Seeding densities for all subsequent experiments (N=3) were $OD_{600}$=0.05. Cells were grown in Yeast Nitrogen Base supplemented with 1 M Phosphate buffer and acetyl-D-glucosamine (YNB-NP) along with appropriate volumes of test compound to provide the desired concentration. Cells were cultured in 96 well plates for 1 hr at 37° C. to facilitate yeast attachment. After this incubation, the supernatants were aspirated, the wells washed twice with YNB-NP media, and fresh media with the same concentration of test compound added to the appropriate wells. The plate was incubated for 24 hr at 37° C. The next day, the cultures were aspirated and the wells washed once with YNB-NP media.

*C. albicans* biofilm quantification was carried out in 96 well plates using a semi-quantitative Tetrazolium salt, 2,3-bis-(2-methoxy-4-nitro-5-sulfophenyl)-2H tetrazolium-5-carboxanilide inner salt (XTT) reduction assay (Hawser, Tunney et al, Antimicrob Agents Chemother. 2004 May; 48(5):1879-81). XTT (0.01 g) was dissolved in sterile water (20 ml) and filter sterilized. 10 μl of Menadione dissolved in Acetone was added to the XTT solution, just before use. The XTT-Menadione Solution (100 μl) was added to each well. The plate was incubated in the dark at 37° C. for up to 2 hr to allow for colour development. The $OD_{492\,nm}$ was recorded for each well. Experiments were repeated at least three times, with at least eight technical replicates.

For the microscopy experiments *C. albicans* biofilms were grown on glass coverslips in 6 well plates, using the biofilm formation protocol above. Briefly, an overnight culture of *C. albicans* was added to YNB-NP media to give an $OD_{600}$=0.05. Test compounds were added at appropriate concentrations. The 6 well plates were incubated at 37° C. for 1 hr to facilitate attachment after which they were washed once in YNB-NP and then fresh test compound in YNB-NP added. Plates were incubated overnight at 37° C. Next day, glass coverslips were washed once in YNB-NP and stained. Calcofluor (1 mg/ml) and 10% (w/v) potassium hydroxide were added drop-wise to coverslips, washed in PBS and viewed. Concavalin A and FUN-1 were added at 50 μg/ml in 1 ml PBS and incubated at 37° C. for 30 mins. Coverslips were washed in PBS and viewed. All imaging was carried out on a Zeiss LSM5 confocal microscope. Confocal images were recorded under a bright field lens using ×20 objective magnification. Filter cubes facilitating fluorescent imaging were used to record images for Calcofluor at 405 nm, Con A at 488 nm and FUN-1 at 543 nm. All images were captured using the Zeiss HBO-100 microscope illuminating system, processed using the Zen AIM application imaging program and converted to JPGs using Axiovision 40 Ver. 4.6.3.0. A minimum of three independent biological repetitions were carried out.

Experiments were first carried out using the test compound at concentration of 100 μM.

FIG. 1 shows graphically the XTT results for compounds B1, B2, methanol (i.e. the solvent alone) and untreated biofilms.

Figure 2:
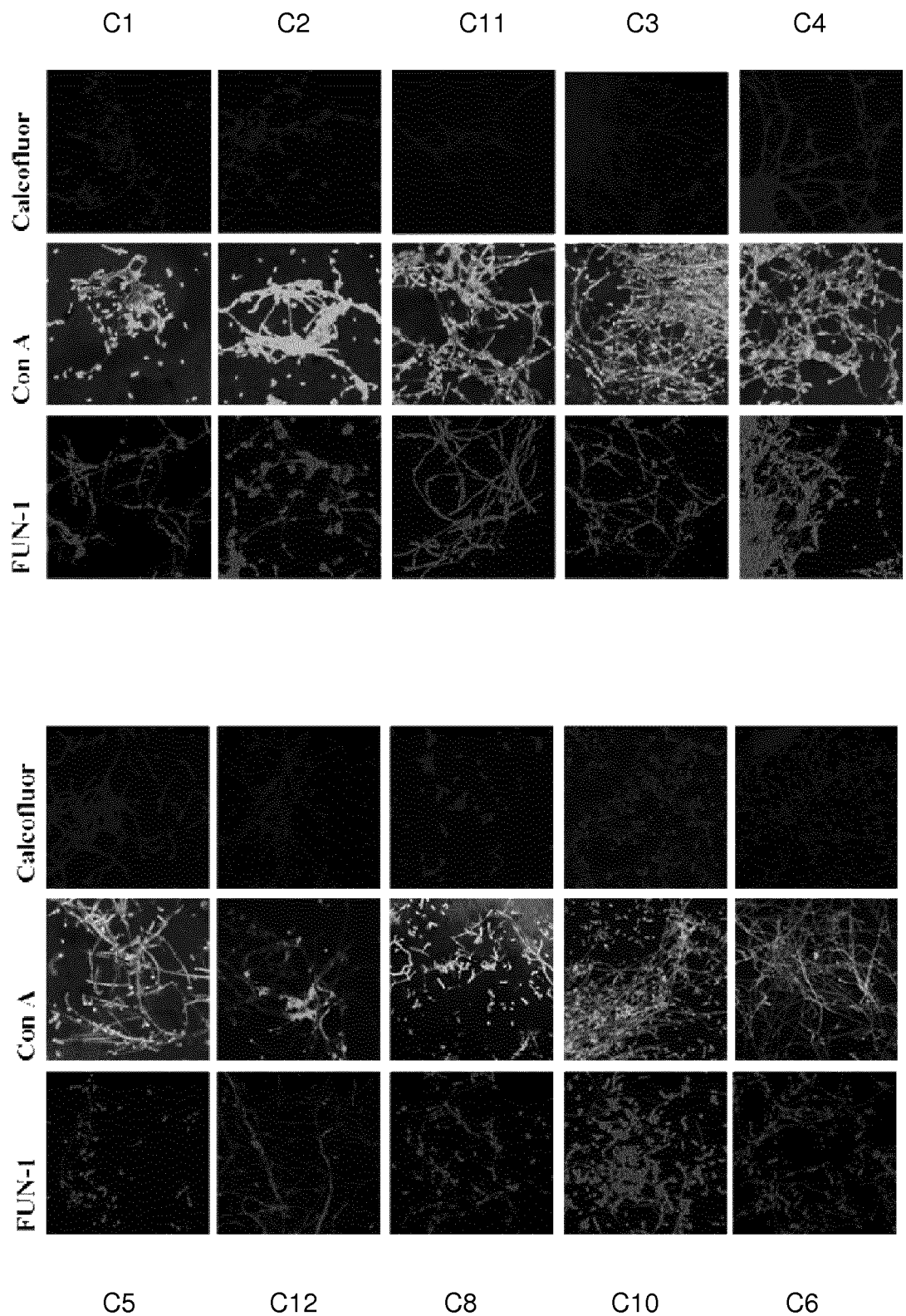
FIG. 2 shows the microscopy results for compounds C1, C2, C3, C4, C5, C6, C8, C10, C11 and C12.

FIG. 2 shows the microscopy results for compounds C1, C2, C3, C4, C5, C6, C8, C10, C11 and C12. The results of the XTT tests for these compounds are detailed in table 1:

TABLE 1

| Compound | Absorbance at 492 nm | |
|---|---|---|
| | Mean | Standard deviation |
| Untreated | 0.851 | 0.079 |
| MeOH (control) | 0.647 | 0.007 |
| B1 | 0.200 | 0.027 |
| B2 | 0.999 | 0.120 |
| C1 | 0.162 | 0.021 |
| C2 | 0.178 | 0.003 |
| C3 | 0.307 | 0.062 |
| C4 | 0.302 | 0.054 |
| C5 | 0.242 | 0.029 |
| C6 | 0.336 | 0.067 |
| C8 | 0.457 | 0.014 |
| C10 | 0.419 | 0.001 |
| C11 | 0.242 | 0.041 |
| C12 | 0.298 | 0.029 |

The above experiments were repeated, this time using concentrations of test compound of 100 μM, 50 μM and 10 μM to show that the compounds can still be effective at lower concentrations. The results are shown in table 2.

TABLE 2

| Compound | | Mean | Standard Deviation |
|---|---|---|---|
| MeOH (control) | | 1 | 0 |
| B1 | | 0.45 | 0.047 |
| B2 | | 1.2 | 0.005 |
| C1 | 10 μM | 0.93 | 0.011 |

TABLE 2-continued

| Compound | | Mean | Standard Deviation |
|---|---|---|---|
| C2 | 10 μM | 0.68 | 0.081 |
| C3 | 10 μM | 0.71 | 0.024 |
| C4 | 10 μM | 0.86 | 0.018 |
| C10 | 10 μM | 0.58 | 0.006 |
| C1 | 50 μM | 0.72 | 0.011 |
| C2 | 50 μM | 0.38 | 0.061 |
| C3 | 50 μM | 0.57 | 0.001 |
| C4 | 50 μM | 0.67 | 0.051 |
| C10 | 50 μM | 0.50 | 0.010 |
| C1 | 100 μM | 0.58 | 0.001 |
| C2 | 100 μM | 0.25 | 0.055 |
| C3 | 100 μM | 0.51 | 0.010 |
| C4 | 100 μM | 0.58 | 0.040 |
| C10 | 100 μM | 0.53 | 0.114 |

EXAMPLE 3

The cytotoxicity of compounds B1, B2, C2, C3, C4, C5, C6 and C12 was tested according to the following method:

Lactate dehydrogenase (LDH) release from IB3 lung epithelial cells was assayed as a measure of cytotoxicity using an LDH colorimetric kit (Roche) according to manufacturers' instructions. Briefly, IB3-1 cells were seeded onto 96 well plates and treated with methanol (control) and test compounds (100 μM). Following 16 hr incubation at 37° C. and 5% $CO_2$, supernatants were removed and added to catalyst reaction mixture in a fresh plate and further incubated at 37° C. and 5% $CO_2$ for 30 mins to allow for colour development. After this period, the plate was analysed on an ELISA plate reader at $OD_{490\,nm}$. Cytotoxicity was expressed as a percentage of cells treated with 0.1% (v/v) Triton (100% cytotoxicity). The results are detailed in table 3:

TABLE 3

| Compound | % Cytotoxicity | |
|---|---|---|
| | Mean | Standard deviation |
| MeOH | 3.844 | 1.40 |
| B1 | 38.93 | 10.89 |
| B2 | 13.84 | 4.18 |
| C2 | 28.94 | 6.76 |
| C3 | 23.77 | 3.46 |
| C4 | 15.46 | 4.35 |
| C5 | 31.04 | 7.74 |
| C6 | 19.70 | 10.20 |
| C12 | 16.68 | 3.97 |

The above experiments were repeated, testing some compounds against further cell lines (A549, DU145 and HeLa). The results are detailed in table 4:

TABLE 4

| | | Cytotoxicity | |
|---|---|---|---|
| Cell Line | Compound | Mean | Standard Deviation |
| A549 | C1 | 8.739 | 1.046 |
| A549 | C12 | 32.37 | 6.63 |
| DU145 | C1 | 6.26 | 4.52 |
| DU145 | C3 | 32.42 | 14.27 |
| DU145 | C4 | 24.42 | 6.49 |
| DU145 | C12 | 8.28 | 1.43 |

TABLE 4-continued

| | | Cytotoxicity | |
|---|---|---|---|
| Cell Line | Compound | Mean | Standard Deviation |
| DU145 | C10 | 31.7 | 5.43 |
| HeLa | C1 | 15.96 | 11.59 |
| HeLa | C12 | 34.57 | 19.08 |

EXAMPLE 4

The virulence of compounds B1, B2, C2, C3, C4, C5, C6, C8 and C11 towards *P. aeruginosa* was assessed using the following method:
RNA Isolation and qRT-PCR Transcriptional Analysis.

Overnight *Candida albicans* cultures were diluted to 0.05 at $OD_{600}$ in either YNB or YNB-NP (Difco). YNB cultures were supplemented with methanol whereas YNB-NP cultures were supplemented with either 10 mM HHQ or the methanol volume equivalent. Cultures were grown at 30° C. with agitation (180 rpm) for 6 hours after which they were centrifuged at 4000 rpm, supernatants discarded and pellets frozen at −20° C. until processing. RNA was isolated using the MasterPure Yeast RNA purification kit (Cambio Ltd, Cambridge UK) according to manufacturer's specifications, and was quantified using a ND-1000 Spectrophotometer (NanoDrop Technologies, USA). Genomic DNA was enzymatically removed using Turbo DNA-free DNase (Ambion), and samples were confirmed DNA free by PCR. RNA was converted to cDNA using random primers and AMV reverse transcriptase (Promega) according to manufacturer's instructions. qRT-PCR was carried out using the Universal ProbeLibrary (UPL) system (Roche) according to manufacturer's specifications, and samples were normalised to *C. albicans* actin transcript expression (ACT1).
Phenazine Extraction.

*P. aeruginosa* strains were cultured as described above for 24 hr, with the addition of test compounds (10 µM). Cultures were centrifuged at 4000 rpm for 10 minutes and the cell free supernatant (5 ml) removed. Chloroform (3 ml) was added, and mixed by vortex. After centrifugation at 4000 rpm for 5 mins, the lower aqueous phase was transferred to 0.2 M HCl (2 ml). Samples were mixed by vortex and centrifuged at 4000 rpm for 5 mins to separate the phases. An aliquot of the top phase (1 ml) was removed and spectrophotmetrically analysed at $OD_{570\ nm}$. Phenazine production was calculated using the following formula: $OD_{570\ nm} \times 2 \times 17.072$ and the units expressed in µg/ml.
Promoter Fusion Based Expression Analysis.

Promoter fusion analyses were performed in a 96-well format. Briefly, overnight cultures of wild-type PAO1 pqsA-lacZ (pLP0996) and mutant strain PAO1 pqsA⁻ pqsA-LacZ were diluted to $OD_{600\ nm}$=0.02 in LB. Test compounds at 100 µM final concentration were added, mixed, aliquoted into 96 well plates and incubated overnight at 37° C. with shaking. The next day, $OD_{600\ nm}$ values were recorded in a plate reader. Aliquots of cells (0.02 ml) were permeabilised [100 mM dibasic sodium phosphate ($Na_2HPO_4$), 20 mM KCl, 2 mM $MgSO_4$, 0.8 mg/mL CTAB (hexadecyltrimethylammonium bromide), 0.4 mg/mL sodium deoxycholate, 5.4 µL/mL beta-mercaptoethanol] and added to substrate solution [60 mM $Na_2HPO_4$, 40 mM $NaH_2PO_4$, 1 mg/mL o-nitrophenyl-β-D-Galactoside (ONPG), 2.7 µL/mL β-mercaptoethanol]. The kinetics of colour development was monitored and the reactions were stopped using 1M $NaCO_3$. $OD_{420\ nm}$ were recorded as above. Miller units were calculated using the following equation; $1000 \times [OD_{420\ nm}/(OD_{600\ nm}) \times 0.02\ ml \times reaction\ time\ (mins)]$.

The phenazine production levels and Miller units in the PAO1 pqsA-pqsA-lacZ strain are detailed in table 5.

TABLE 5

| | Phenazine (µg/ml) | | Miller Units | |
|---|---|---|---|---|
| Compound | Mean | Standard deviation | Mean | Standard deviation |
| Untreated | 0.224 | 0.525 | 11711 | 4153 |
| Methanol control | 0.080 | 0.131 | 12287 | 4283 |
| Water control | 3.088 | 0.799 | — | — |
| B1 | 2.697 | 0.537 | 65076 | 27746 |
| B2 | 2.117 | 0.727 | 61429 | 28389 |
| C2 | 0.541 | 0.497 | 16027 | 4749 |
| C3 | 0.774 | 0.523 | 18350 | 4331 |
| C4 | 0 | 0 | 35489 | 12432 |
| C5 | 0 | 0 | 11940 | 691 |
| C6 | 0.011 | 0.019 | 16678 | 9700 |
| C8 | 0.205 | 0.354 | 11753 | 1695 |
| C11 | 0.432 | 0.603 | 12254 | 1913 |

The virulence of compounds B2, C13 and C15 towards *P. aeruginosa* was assessed using an analogous method. The results are shown in table 6:

TABLE 6

| | Normalised Phenazine (µg/ml) | | Normalised Miller Units | |
|---|---|---|---|---|
| Compound | Mean | Standard Deviation | Mean | Standard Deviation |
| Methanol control | 1 | | 1 | |
| DMSO control | 1.32174 | 0.522353 | 1.44997 | 1.08499 |
| B2 | 4.196486 | 1.802723 | 3.078914 | 0.850754 |
| C13 | 0.747026 | 0.160539 | 0.371541 | 0.173011 |
| C15 | 0.498371 | 0.319781 | 0.467063 | 0.154079 |

Data (a minimum of n=2 for each datapoint) is presented normalized to the methanol control.

EXAMPLE 5

The ability of some of the compounds detailed in example 1 to disrupt *Aspergillus fumigatus* was tested.
*Aspergillus fumigatus* Stock Maintenance and Culturing Conditions.

*A. fumigatus* Af293 was routinely grown on Sabouraud dextrose agar (SDA) in 100 ml cell culture flasks at 37° C. for 3-4 days until a lawn of fungal growth was observed.
Spore Capture and Biofilm Assay

*A. fumigatus* Af293 was grown on SDA in 100 ml cell culture flasks at 37° C. for 3-4 days. Conidia were harvested by flooding the surface of the agar plates with 5 ml PBS (Oxoid) containing 0.025% (v/v) Tween 20 and gently moving the liquid over the surface of the fungal lawn. The conidial suspension was transferred into a 25 ml sterile container and conidia were counted using a Neubauer haemocytometer and light microscope. Conidia were adjusted to the required concentration in RPMI 1640 (Sigma) buffered to pH 7.0 with 0.165 M MOPS immediately prior to biofilm formation analysis.

To assess biofilm formation, counted *A. fumigatus* spores $(1 \times 10^5)$ in MOPS buffered RPMI 1640 were inoculated into 24- and 96-well plates and grown overnight in the presence of 100 µM HHQ, PQS and the test compounds. After 24 hrs, the media was removed and the biofilm washed twice with distilled water after which 0.1% crystal violet (CV) was added to each well and allowed to stand for 1 hr at room temperature. The crystal violet was removed and all wells washed in a water bath by inversion. Ethanol was added to each well to solubilise biofilms after which samples were read on a spectrophotometer at $Abs_{595\ nm}$.

Staining and Microscopy

*A. fumigatus* spores ($1 \times 10^5$) were inoculated onto glass coverslips in 24 well plates and grown in the presence of analogues overnight at 37° C. in RPMI buffered with MOPS pH 7.0. After 24 hrs, glass coverslips were washed once in PBS and stained. Staining and microscopy was performed as described in Example 2.

Figure 3:
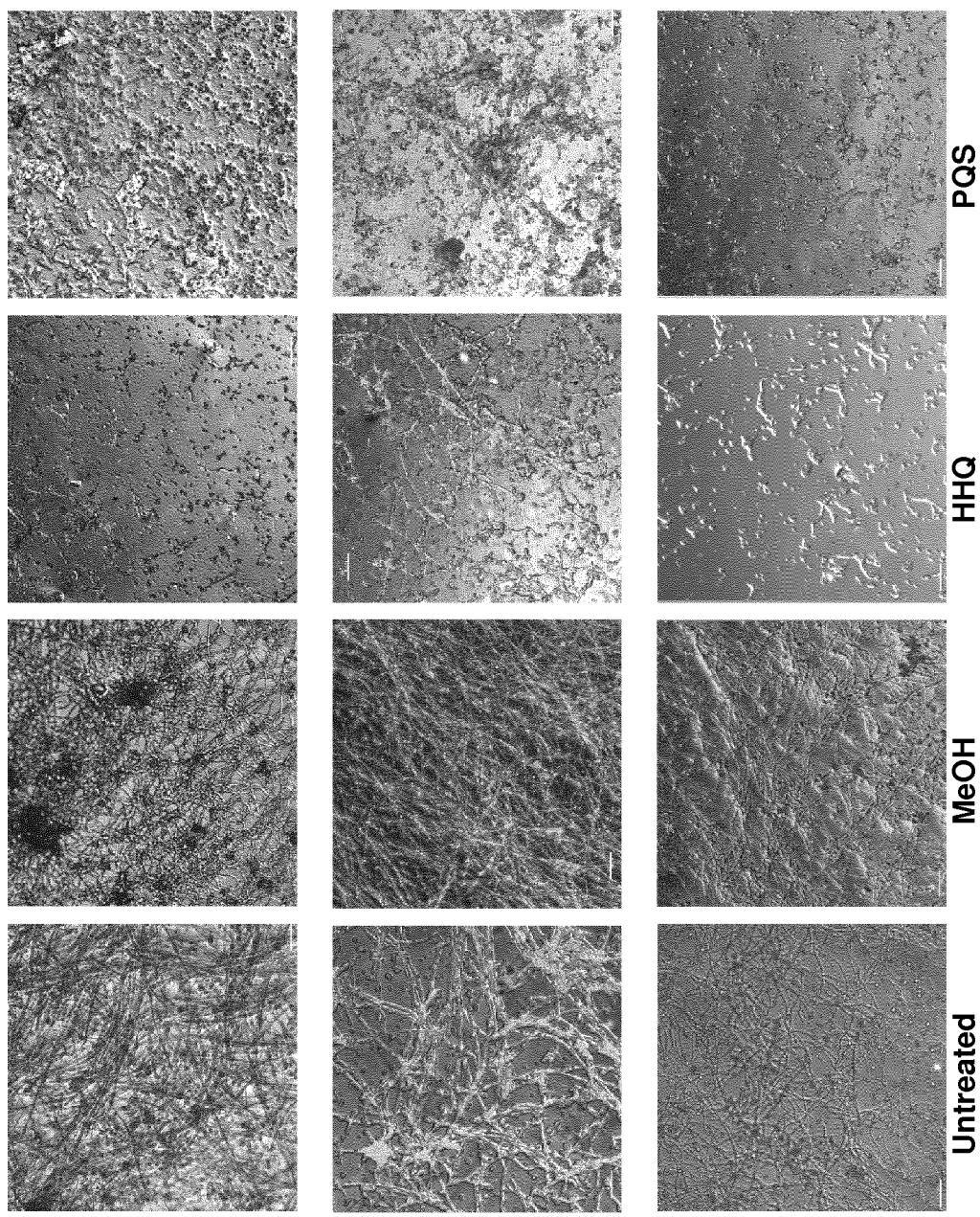
FIG. 3 shows the microscopy results for compounds B1, B2, methanol and untreated biofilms.

FIG. 3 shows the microscopy results for compounds B1, B2, methanol and untreated biofilms.

Figure 4:
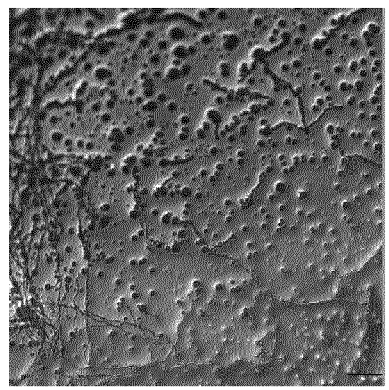
FIG. 4 shows the microscopy results for compounds C1, C2, C7, C8, C9 and C10.
Figure 4:
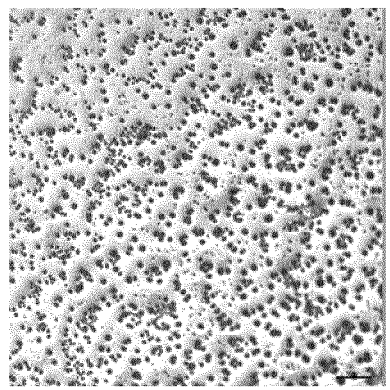
Figure 4:
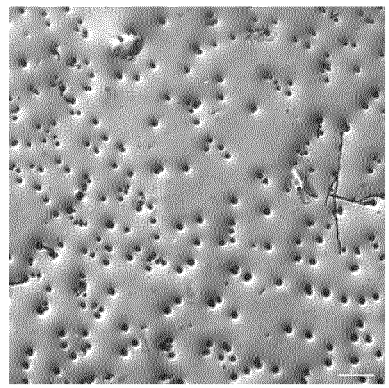
Figure 4:
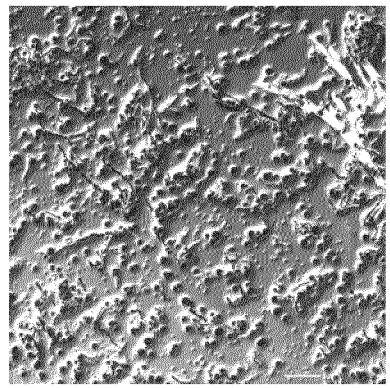
Figure 4:
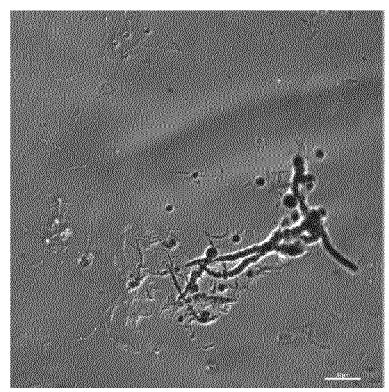
Figure 4:
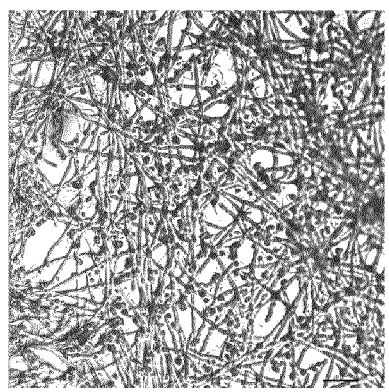

FIG. 4 shows the microscopy results for compounds C1, C2, C7, C8, C9 and C10. The results of the XTT tests are detailed in table 7:

TABLE 7

| Compound | Relative absorbance at 595 nm compared to methanol control | |
|---|---|---|
| | Mean | Standard deviation |
| Methanol | 1 | 0 |
| C1 | 0.39 | 0.18 |
| C2 | 0.37 | 0.10 |
| C7 | 0.27 | 0.14 |
| C8 | 0.47 | 0.16 |
| C9 | 0.18 | 0.05 |
| C10 | 0.24 | 0.12 |
| C13 | 0.38 | 0.09 |
| C14 | 0.42 | 0.21 |
| C15 | 0.25 | 0.10 |

The above experiments were carried out using biofilms grown from laboratory sources of *A. fumigatus*. The experiments were repeated to test some compounds against biofilms grown from three different clinical sources of *A. fumigatus* (CFBRC1, CFBRC2 and CFBRC3. The results are shown in table 8:

TABLE 8

| Compound | | Mean | Standard Deviation |
|---|---|---|---|
| CFBRC1 | C1 | 0.432 | 0.091 |
| CFBRC1 | C2 | 0.310 | 0.190 |
| CFBRC1 | C5 | 0.297 | 0.171 |
| CFBRC1 | C9 | 0.593 | 0.126 |
| CFBRC1 | C10 | 0.772 | 0.267 |
| CFBRC1 | C13 | 0.507 | 0.181 |
| CFBRC1 | C14 | 0.550 | 0.068 |
| CFBRC1 | C15 | 0.518 | 0.287 |
| CFBRC1 | B1 | 0.412 | 0.160 |
| CFBRC1 | B2 | 0.561 | 0.325 |
| CFBRC1 | MeOH | 1 | 0 |
| CFBRC2 | C1 | 0.497 | 0.147 |
| CFBRC2 | C2 | 0.304 | 0.147 |
| CFBRC2 | C5 | 0.359 | 0.170 |
| CFBRC2 | C9 | 0.484 | 0.040 |
| CFBRC2 | C10 | 0.567 | 0.157 |
| CFBRC2 | C13 | 0.620 | 0.088 |
| CFBRC2 | C14 | 0.823 | 0.246 |
| CFBRC2 | C15 | 0.443 | 0.280 |
| CFBRC2 | B1 | 0.509 | 0.204 |
| CFBRC2 | B2 | 0.673 | 0.274 |
| CFBRC2 | MeOH | 1 | 0 |
| CFBRC3 | C1 | 0.471 | 0.182 |
| CFBRC3 | C2 | 0.292 | 0.161 |
| CFBRC3 | C5 | 0.483 | 0.247 |
| CFBRC3 | C9 | 0.439 | 0.129 |
| CFBRC3 | C10 | 0.670 | 0.018 |
| CFBRC3 | C13 | 0.609 | 0.108 |
| CFBRC3 | C14 | 0.501 | 0.073 |
| CFBRC3 | C15 | 0.413 | 0.217 |
| CFBRC3 | B1 | 0.484 | 0.187 |
| CFBRC3 | B2 | 0.546 | 0.338 |
| CFBRC3 | MeOH | 1 | 0 |

EXAMPLE 6

The anti biofilm properties of some of the claimed compounds was tested by carrying out a viable biofilm assay and measuring the growth of the microbes.

Viable Colony Biofilm Assay

*C. albicans* biofilms, supplemented with test and comparative compounds, were grown in 6-well plates and incubated overnight at 37° C. Briefly, *C. albicans* Yeast Nitrogen Base (YNB) cultures were measured at OD600 nm, diluted to 0.05 in YNB-NP supplemented with analogues, plated onto 6-well plates and incubated for 1 hr at 37° C. Media was removed, wells were washed twice with sterile PBS and supplemented with fresh YNB-NP with analogues. Plates were incubated overnight at 37° C. after which media was removed and wells washed with sterile PBS. For serial dilutions, biofilms were cell-scraped into 1 ml PBS, vortexed, and serially diluted into sterile PBS. Serial 147 dilutions were plated (100 µl) onto YPD agar and incubating overnight at 37° C. Colonies were counted and recorded the next day.

*C. albicans* Growth Curves

Overnight *C. albicans* cultures grown in YNB were diluted to 0.05 in YNB supplemented with analogues. Cultures (200 µl) were added to each well of a 100 well plate and grown for a 24 hr period on a Bioscreen C spectrophotometer (Growth Curves USA).

Figure 5A:
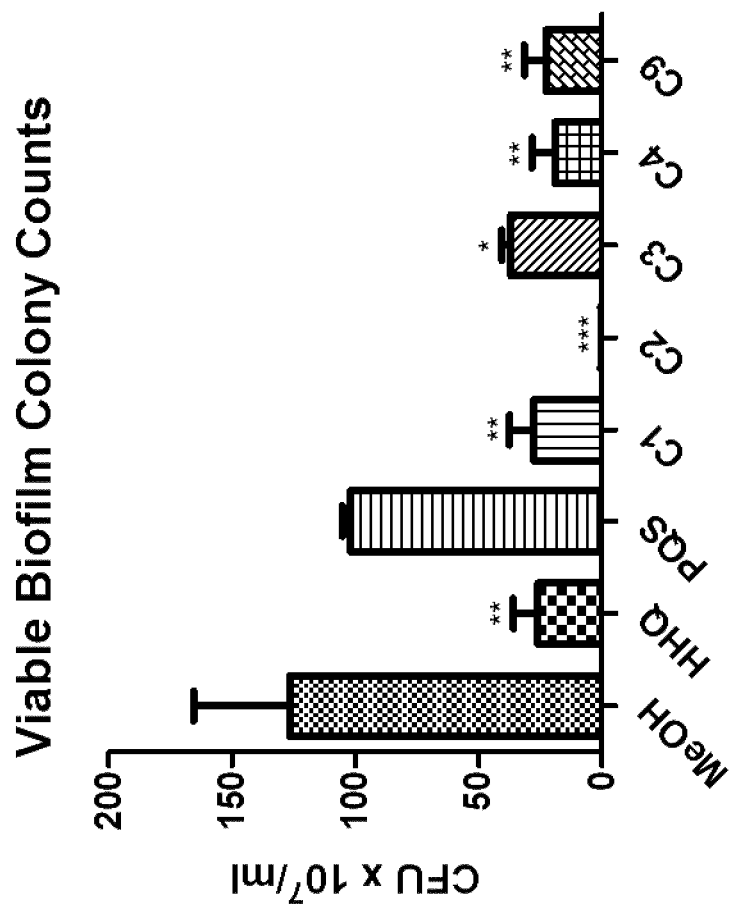
FIG. 5A and FIG. 5B demonstrate how the compounds interrupt the biofilm rather than simply inhibiting growth.
Figure 5B:
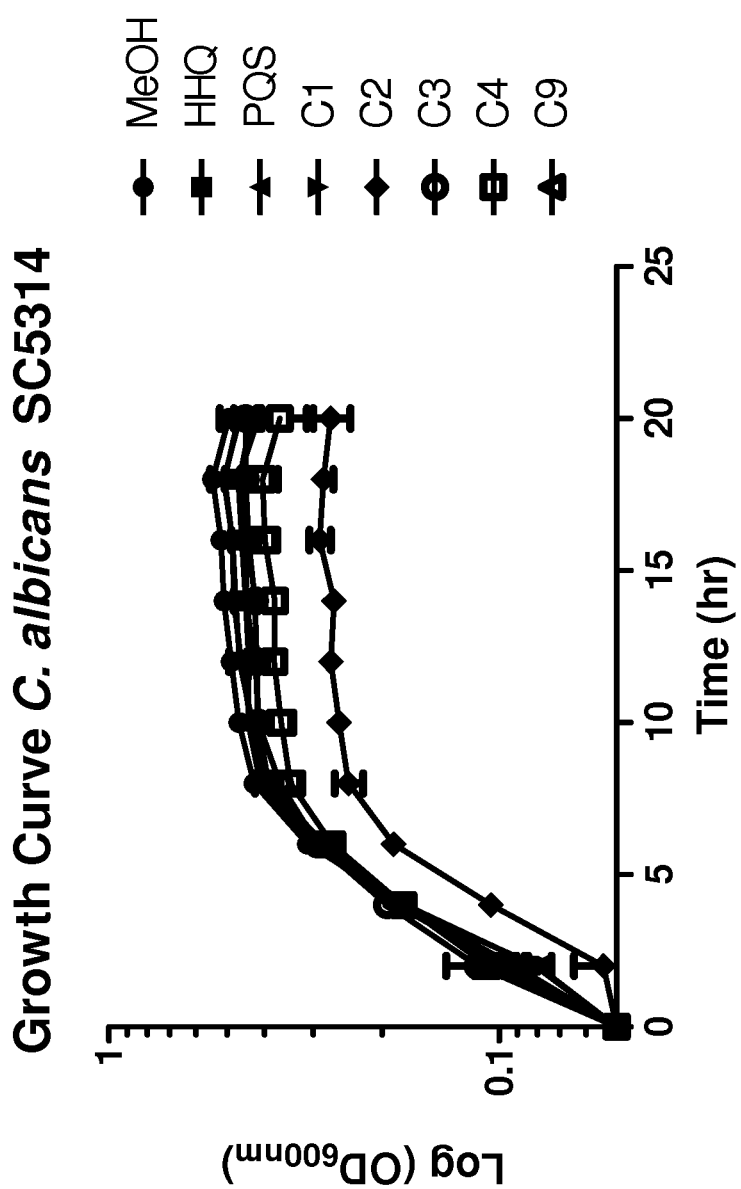

The results, shown in FIGS. 5A and 5B demonstrate how the compounds interrupt the biofilm rather than simply inhibiting growth.

The invention claimed is:

1. An antibiofilm composition comprising a compound of formula (A2):

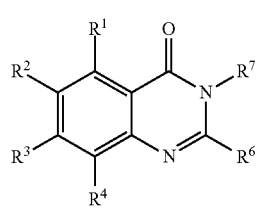

(A2)

wherein each of $R^1$, $R^2$, $R^3$, $R^4$, $R^5$, $R^6$ and $R^7$ is independently selected from hydrogen, alkyl, alkenyl, aryl, halo, alkoxy, hydroxyl, amino, nitro, sulfoxy, thiol, carboxy, alkyl carboxy and amido; and X may be O or S, wherein the composition does not comprise a compound of formula (B1) or (B2):

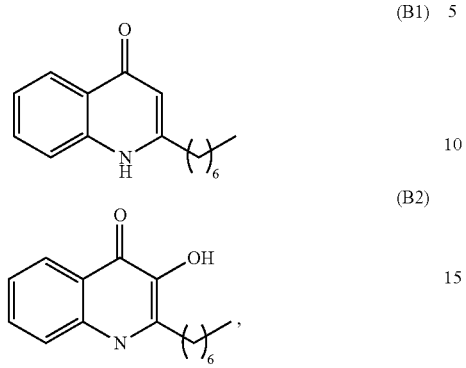

wherein the composition is effective against biofilms formed by fungi, and is a pharmaceutical preparation that further comprises one or more additional antifungal agents.

2. The composition of claim 1, wherein the composition disrupts or removes fungal biofilms or inhibits or prevents the growth of fungal biofilms.

3. The composition of claim 1, wherein the composition is effective against biofilms containing a single fungal species, multiple fungal species, or one or more fungal species and one or more species of bacteria.

4. The composition according to claim 1 comprising a compound of formula (A2) wherein $R^1$ is hydrogen; $R^2$ is hydrogen; $R^3$ is hydrogen; $R^4$ is hydrogen; $R^6$ is $C_7$ to $C_9$ alkyl; and $R^7$ is hydrogen or amino.

5. The composition of claim 1 which is effective against *Candida albicans* and/or *Aspergillus fumigatus*.

6. The composition according to claim 1 which is effective against *Candida albicans* and includes
a compound of formula (A2) wherein $R^1$ is hydrogen; $R^2$ is hydrogen; $R^3$ is hydrogen; $R^4$ is hydrogen; $R^6$ is $C_7$ alkyl and $R^7$ is hydrogen or amino.

7. The composition according to claim 1 which is effective against *Aspergillus fumigatus* and includes
a compound of formula (A2) wherein $R^1$ is hydrogen; $R^2$ is hydrogen; $R^3$ is hydrogen; $R^4$ is hydrogen; $R^6$ is $C_7$ alkyl and $R^7$ is hydrogen or amino.

8. An antibiofilm composition comprising a compound of formula (A2):

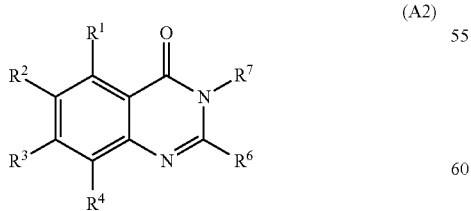

wherein each of $R^1$, $R^2$, $R^3$, $R^4$, $R^5$, $R^6$ and $R^7$ is independently selected from hydrogen, alkyl, alkenyl, aryl, halo, alkoxy, hydroxyl, amino, nitro, sulfoxy, thiol, carboxy, alkyl carboxy and amido; and X may be O or S, wherein the composition does not comprise a compound of formula (B1) or (B2):

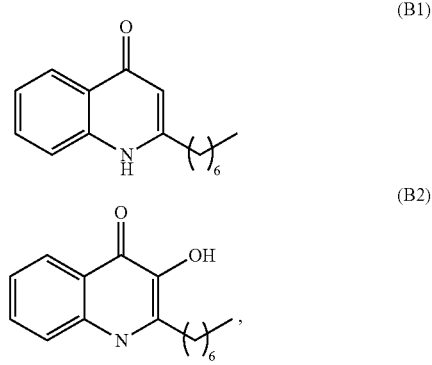

which composition is effective against biofilms formed by fungi and is a contact lens solution that further comprises one or more additional antifungal agents.

9. The composition according to claim 8 comprising a compound of formula (A2) wherein $R^1$ is hydrogen; $R^2$ is hydrogen; $R^3$ is hydrogen; $R^4$ is hydrogen; $R^6$ is $C_7$ to $C_9$ alkyl; and $R^7$ is hydrogen or amino.

10. The composition according to claim 8 which is effective against *Candida albicans* and/or *Aspergillus fumigatus*.

11. The composition according to claim 8 which is effective against *Candida albicans* and includes a compound of formula (A2) wherein $R^1$ is hydrogen; $R^2$ is hydrogen; $R^3$ is hydrogen; $R^4$ is hydrogen; $R^6$ is $C_7$ alkyl and $R^7$ is hydrogen or amino.

12. The composition according to claim 8 which is effective against *Aspergillus fumigatus* and includes a compound of formula (A2) wherein $R^1$ is hydrogen; $R^2$ is hydrogen; $R^3$ is hydrogen; $R^4$ is hydrogen; $R^6$ is $C_7$ alkyl and $R^7$ is hydrogen or amino.

13. A medical device having a coating on at least a portion thereof; wherein the coating comprises an antibiofilm compound of formula (A2):

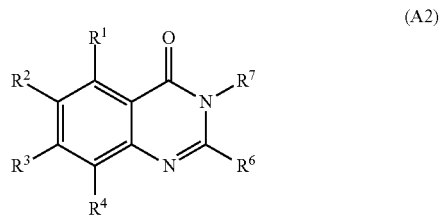

wherein each of $R^1$, $R^2$, $R^3$, $R^4$, $R^5$, $R^6$ and $R^7$ is independently selected from hydrogen, alkyl, alkenyl, aryl, halo, alkoxy, hydroxyl, amino, nitro, sulfoxy, thiol, carboxy, alkyl carboxy and amido; and X may be O or S, wherein the composition does not comprise a compound of formula (B1) or (B2):

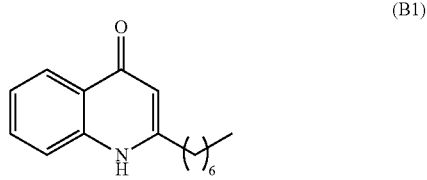

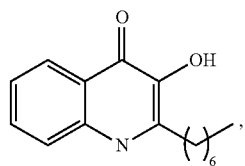
wherein the composition is effective against biofilms formed by fungi.
* * * * *